United States Patent [19]

Jaxa-Chamiec et al.

[11] Patent Number: 4,954,339

[45] Date of Patent: Sep. 4, 1990

[54] NOVEL POLYSTYRENE ANION EXCHANGE POLYMERS

[75] Inventors: Albert A. Jaxa-Chamiec, Rickmansworth; Deirdre M. B. Hickey, Saffron Walden, both of England

[73] Assignee: Smith Kline & French Laboratories Limited, Welwyn Garden City, England

[21] Appl. No.: 288,049

[22] Filed: Dec. 21, 1988

[30] Foreign Application Priority Data

Dec. 23, 1987 [GB] United Kingdom ............... 8730010

[51] Int. Cl.$^5$ .................... A61K 31/74; C08C 19/12; C08F 12/36; C08F 112/36

[52] U.S. Cl. ............................. 424/78; 424/79; 424/83; 525/332.2

[58] Field of Search .................... 424/78, 79, 83; 525/332.2

[56] References Cited

U.S. PATENT DOCUMENTS

| | | | |
|---|---|---|---|
| 3,780,171 | 12/1973 | Irmscher et al. | 424/78 |
| 3,898,088 | 8/1975 | Cohen et al. | 430/518 |
| 4,198,395 | 4/1980 | De Simone | 424/79 |
| 4,482,680 | 11/1984 | Sheldon et al. | 525/331.4 |
| 4,510,128 | 4/1985 | Khanna | 424/79 |
| 4,532,128 | 7/1985 | Sheldon et al. | 424/78 |

FOREIGN PATENT DOCUMENTS

| | | |
|---|---|---|
| 929391 | 6/1963 | United Kingdom . |
| 2026501 | 2/1980 | United Kingdom . |

OTHER PUBLICATIONS

Revue Roumaine de Chimie, 25, 145, 1980; I. Petrariu et al.

Makromol. Chem. Suppl. 10/11, 319, (1985); R. A. Wessling et al.

Water, Air & Soil Pollution, (12), 1979, 477–484; Ilona H. Walfish et al.

J. Macromol. Sci. Chem., A22(5–7), pp. 907–929, (1985); A. Carpov, et al.

Chem. Pharm. Bull., 32(3), 823, 1984; Hirofumi Takeuchi et al.

*Primary Examiner*—Joseph L. Schofer
*Assistant Examiner*—Carmen Pili-Curtis
*Attorney, Agent, or Firm*—Stuart R. Suter; Edward T. Lentz

[57] ABSTRACT

Polystyrene polymers having a quaternized ammonium group and their use in a method of treatment of hypercholesterolaemia. A particular compound of the invention is N,N-dimethyl-N-dodecylammoniomethyl-substituted polystyrene.

16 Claims, No Drawings

NOVEL POLYSTYRENE ANION EXCHANGE POLYMERS

The present invention relates to novel polystyrene anion exchange polymers, processes for their preparation, intermediates useful in their preparation, pharmaceutical compositions containing them and their use in the lowering of plasma cholesterol levels in humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange polymers, in particular polystyrene polymers can be used as sequestering agents to bind non-absorbed bile acids and salts in the intestinal tract, forming complexes which are then excreted in the faeces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering polymers have been recognised as useful for the treatment of hypercholesterolaemia, and it is now proven that reducing serum cholesterol with bile acid sequestrants has a beneficial effect on protecting against the occurrence of coronary heart disease.

The polystyrene polymers known in the art to have such sequestering activity are, in general, those bearing a di- or triloweralkyl ammonium group, such as a trimethylammonium group. For example, GB 1286949 discloses a series of macroporous polystyrene polymers having 5-20% cross-link, and GB 1579490 discloses a series of microporous polymers having 8-20% cross-link. In addition, GB 2026501 discloses a series of, inter alia, polystyrene polymers which are said to have particular water absorption capacities, i.e. 69-73% by weight of polymer weight. In each of the foregoing, the polystyrene polymers bear di- or triloweralkyl ammonium groups, in particular a trimethylammonium group.

One particular agent based on a polystyrene polymer which is currently used to lower serum cholesterol levels in humans by binding bile acids in the intestinal tract is cholestyramine (GB 929391). Cholestyramine is a cross-linked anion exchange polystyrene polymer bearing an ionisable trimethylammonium group bound to the polymer backbone. However, the use of this agent is associated with a number of undesirable side-effects, for example, it is unpalatable and must be taken in large doses (up to 36 g per day) and causes, in some cases, bloating, constipation and other gut side-effects. In addition, its ability to bind bile acids is inefficient with respect to the amounts of polymer which it is necessary to use.

It is the object of the present invention to provide compounds which overcome the disadvantages of this known sequestering agent and provide improved bile acid sequestering agents which are useful for lowering serum cholesterol levels in humans.

The present invention therefore provides in a first aspect polystyrene polymers of structure (1):

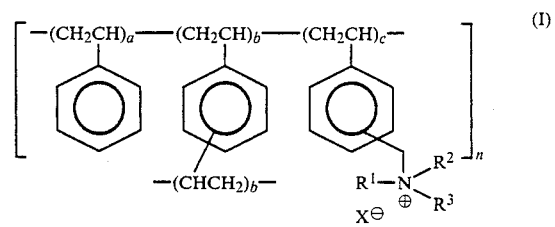

in which, $R^1$ is a saturated or unsaturated $C_6$ to $C_{20}$ alkyl group;

$R^2$ and $R^3$ are the same or different and are each $C_{1-4}$ alkyl;

$X-$ is a physiologically acceptable counter ion;

a, b and c are numbers which indicate the relative molar percentages of the units present in a random distribution in said polymer, (b) being from about 0.5 to about 10 molar percent, and (c) being from about 30 to about 99 molar percent; and n is a number indicating the number of repeating units in said polymer.

Suitably, $R^1$ is a saturated or unsaturated $C_6$ to $C_{20}$ alkyl group. More suitably $R^1$ is a saturated $C_6$ to $C_{20}$ alkyl group. Preferably $R^1$ is a saturated $C_8$ to $C_{14}$ alkyl group; most preferably a $C_{12}$ alkyl group, in particular an unbranched $C_{12}$ alkyl group.

Suitably the groups $R^2$ and $R^3$ are the same or different and are each $C_{1-4}$alkyl; preferably they are the same; most preferably $R^2$ and $R^3$ are both methyl.

Suitably (b) is from about 0.5 to about 10 molar percent of said polymer. Preferably (b) is from about 1 to about 8 molar percent of said polymer; most preferably from about 1 to about 4 molar percent.

Suitably $X-$ is a physiologically acceptable counter ion such as a sulphate, bicarbonate, carbonate, formate, acetate, sulphonate, propionate, malonate, succinate, malate, tartrate, citrate, maleate, fumarate, ascorbate, glucuronate, phosphate, or halide, or the anion of an amino acid such as aspartic or glutamic acid. More suitably $X-$ is a phosphate, sulphate or a halide ion; preferably a halide ion, in particular chloride.

n is a number indicating the number of repeating units in said polymer. Owing to the three dimensional cross-linkage precise figures cannot be given for n, but in any case will be greater than 1,000.

The polystyrene polymers of the present invention are also characterised by their total exchange capacity i.e. the theoretical maximum capacity of the polymer if each counter ion were to be exchanged with bile acid. In this specification the total exchange capacity is defined in terms of the number of milliequivalents of counter ion per gram of dry weight of polymer.

Suitable total exchange capacities are in the range of for example where the counter ion $X-$ is a halide ion such as chlorine, from 1.5 to 3.5 meq $Cl-$ per gram of polymer. Preferred within this range are polymers having a total exchange capacity of between 2 and 3 meq $Cl-$/gram of polymer.

In addition, it is to be noted that the approximate molar percentages (a), (b) and (c) are calculated from the monomer mixture or, in some instances (c) from microanalytical data.

It is to be noted that the term 'bile acid' when used herein shall be taken to include bile acids, bile salts and conjugates thereof.

The polystyrene polymers of the present invention can be prepared by processes analogous to those known in the art. The present invention therefore provides, in a further aspect, a process for preparing the polystyrene polymers of structure (I) which comprises:

(a) reaction of a polymer of structure (II)

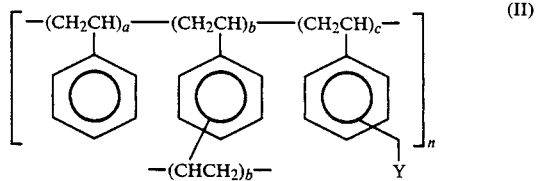

(II)

in which a, b, c and n are as described for structure (I) and Y is a group displaceable by an amine, with an amine of structure $R^1R^2R^3N$ (III) in which $R^1$ to $R^3$ are as described for structure (I);

(b) reaction of a compound of structure (IV)

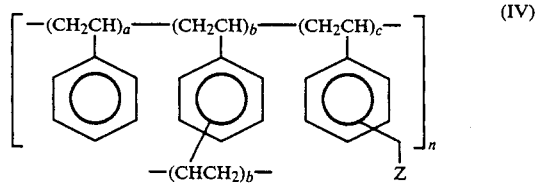

(IV)

in which a, b, c and n are as described for structure (I) and Z is $NR^1R^2$ or $NR^2R^3$ in which $R^1$ to $R^3$ are as described for structure (I), with a compound of structure $R^4Y$ (V) in which $R^4$ is a $C_{1-4}$alkyl group when Z is $NR^1R^2$ or a saturated or unsaturated $C_{6-20}$alkyl group when Z is $NR^2R^3$, and Y is a group displaceable by an amine.

The reaction between a polymer of structure (II) and an amine of structure (III) can be carried out in a suitable solvent at elevated temperature. Suitable solvents include for example, a $C_{1-4}$alkanol, N-methylpyrrolidone, sulpholane, dimethylformamide, nitromethane or tetrahydrofuran. Preferably the reaction is carried out in N-methylpyrrolidone at a temperature of between about 50° and 80° for up to 24 hours or until the reaction is complete.

The reaction between a polymer of structure (IV) and a compound of structure (V) can be carried out in a suitable inert solvent such as a $C_{1-4}$alkanol, nitromethane, sulpholane, N-methylpyrrolidone, dimethylformamide or tetrahydrofuran at elevated temperature.

The intermediate polymers of structure (11) are available commercially or can be prepared from readily available materials by methods known to those skilled in the art. For example polymers of structure (II) in which Y is chlorine can be prepared by reaction of chloromethylstyrene, styrene and divinyl benzene in an aqueous suspension comprising polyvinyl alcohol in the presence of an initiator such as AIBN at elevated temperature.

Alternatively, the intermediate polymers of structure (II) can be prepared directly from polystyrene by methods analogous to those known in the art, for example where Y is chlorine by chloromethylation of polystyrene.

Certain intermediates of structure (IV) are novel and form a further aspect of the invention namely compounds of structure (IVA)

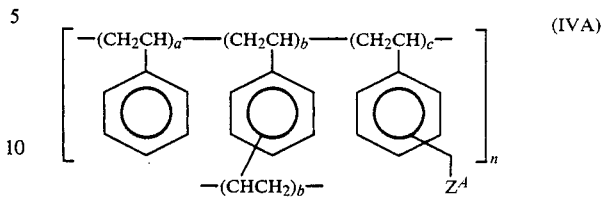

(IVA)

in which a, b, c and n are as described for structure (I) and $Z^A$ is $NR^1R^2$ or $NR^1R^3$ in which $R^1$ to $R^3$ are as described for structure (I).

The intermediate polymers of structure (IV) can be prepared from the polymers of structure (II) by reaction with an amine of structure $R_2NH$ in which $R_2$ is $R^1R^2$ or $R^2R^3$ under the same or similar conditions as indicated for the reaction of a compound of structure (II) and a compound of structure (III).

Alternatively the intermediate polymers of structure (IV) can be prepared by polymerisation of styrene. divinylbenzene and a compound of structure (V)

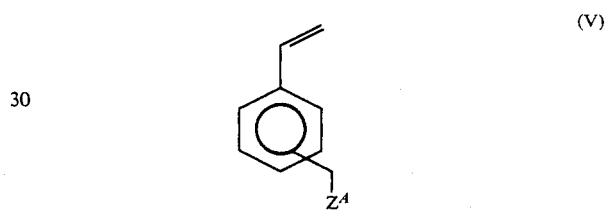

(V)

in which $Z^a$ is as defined in structure (IVA), under standard polymerisation conditions. For example. polymerisation can be carried out in an aqueous suspension comprising, for example, polyvinyl alcohol in the presence of an initiator at elevated temperature. Suitable initiators include, for example, AIBN.

The intermediate compounds of structure (V) can be prepared by reaction of an amine of structure $R_2NH$ in which $R_2$ is $R^1R^2$ or $R^1R^3$ with a corresponding compound of structure (V) in which $Z^a$ is a group displaceable by an amine.

The polystyrene polymers of structure (I) have been found to bind bile acids in in vitro experiments and in in vivo animal models they have been found to increase the amount of bile acids detectable in the faeces. In particular, when compared to the known sequestrants e.g. cholestyramine, the polymers of structure (1) haVe surprisingly been found to have an unexpected profile of activity which is thought will provide advantages over the known compounds in the lowering of serum cholesterol levels in animals, in particular humans. More specifically, in in vitro experiments, when compared to cholestyramine the compounds of structure (I) have been found to bind comparable amounts of bile acid per gram of polymer (at physiological concentrations of bile acids), and to bind the bile acid more strongly i.e., the bile acids have been found to dissociate more slowly from the compounds of the invention. It is expected that compounds having such qualities will be able to achieve significant lowering of plasma cholesterol levels at much lower dosages than has hitherto been possible with known sequestrants (currently given at up to 36 g/day).

As indicated earlier it is recognised that removal of bile acids from the intestinal tract in this way lowers serum cholesterol levels and also has a beneficial effect on protecting against atherosclerosis and its dependent clinical conditions. The present invention therefore provides in a further aspect, polystyrene polymers of structure (I) for use in therapy, in particular for the lowering of serum cholesterol levels in mammals, including humans. In addition the polymers of structure (I) are expected to be of use in protecting against atherosclerosis and its sequelae, and for example in the treatment of pruritus and diarrhoea.

In view of the foregoing the present invention also provides a method of lowering serum cholesterol levels in mammals which comprises administering to a mammal in need thereof an effective serum cholesterol lowering amount of a polystyrene polymer of structure (I); and a method of protecting against atherosclerosis.

When used in therapy in the methods of the invention, the polystyrene polymers of structure (I) are in general administered in a pharmaceutical composition.

In a still further aspect of the present invention there is therefore provided a pharmaceutical composition comprising a polystyrene polymer of structure I) in association with a pharmaceutically acceptable carrier.

The compositions of the present invention can be prepared by techniques well known to those skilled in the art of pharmacy and include all those known for the formulation of polystyrene polymers for human use.

The polymers are preferably administered as formulations in admixture with one or more conventional pharmaceutical excipients which are physically and chemically compatible with the polymer, which are nontoxic, are without deleterious side-effects but which confer appropriate properties on the dosage form.

In general, for liquid formulations, aqueous based pharmaceutically acceptable carriers such as water itself or aqueous dilute ethanol, propylene glycol, polyethylene glycol or glycerol or sorbitol solutions are preferred. Such formulations can also include preservatives and flavouring and sweetening agents such as sucrose, fructose, invert sugar, cocoa, citric acid, ascorbic acid, fruit juices etc. In general, digestible oil or fat based carriers should be avoided or minimised as they contribute to the condition sought to be alleviated by use of the polymers. They are also subject to absorption by the polymers during prolonged contact, thus reducing the capacity of the polymer to absorb bile acids after administration.

The polymers can also be prepared as 'concentrates', for dilution prior to administration, and as formulations suitable for direct oral administration. They can be administered orally ad libitum, on a relatively continuous basis for example by dispersing the polymer in drinks or food.

Preferably, the polymers are administered in tablet form or in gelatin capsules containing solid particulate polymer or a non-aqueous suspension of solid polymer containing a suitable suspending agent. Suitable excipients for such formulations will be apparent to those skilled in the art and include, for example, for tablets and capsules lactose, microcrystalline cellulose, magnesium stearate, povidone, sodium starch glycollate and starches: and for suspensions in capsules, polyethylene glycol, propylene glycol and colloidal silicon dioxide.

Preferably the polymer is administered in unit dosage form, each dosage unit containing preferably from 0.3 g to 1 g of polymer.

The daily dosage regimen for an adult patient may be, for example, a total daily oral dose of between 1 and 10 g preferably 1–5 g, the compound being administered 1 to 4 times a day depending on the size of individual dosage units. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following data and examples indicate the properties and preparation of the polymers of the present invention. Temperatures are recorded in degrees celsius. The exchange capacity of the ammonium substituted polymers was determined by elemental analysis and/or potentiometric titration of chloride ion. Figures quoted are expressed as milliequivalents of exchangeable chloride ion per gram of dry polymer weight.

Chloromethylstyrene was used as a 60:40 m:p mixture and was washed free of inhibitor before use.

Divinylbenzene (DVB) was used as a 55% mixture with ethylstyrene and the weights given are that of the mixture. The percent cross-link given is based on the percent of divinylbenzene (not the mixture) calculated to be in the monomer mixture. The molar percent of divinylbenzene (b) quoted is based on the molar percent of DVB in the monomer mixture.

EXAMPLE 1

Chloromethylstyrene (60:40 m.p. mixture) (26.7 g), styrene (22.4 g), divinylbenzene (0.91 g), and azobisisobutyronitrile (AIBN) (0.5 g) were mixed to give a homogenous solution and added to a solution of poly(vinyl alcohol) (m.w. 125,000) (1.0 g) in distilled water (500 ml). The mixture was then stirred at 80° under an atmosphere of nitrogen at such a rate as to maintain the monomers in suspension. After 7 hours the stirring was stopped and the mixture poured into distilled water. The resin formed was washed by decantation with cold and hot water, filtered, and washed with acetone, tetrahydrofuran, and acetone, and dried to give a 1% cross-linked chloromethyl-substituted polystyrene containing 3.3 m.eq. Cl/g (36.6 g). This polymer was then sieved and the 53–106 $\mu$M fraction (15.8 g) used in further reactions.

This fraction of the chloromethylated polystyrene (3.3 g) was suspended in N N-dimethylformamide (DMF) (65 ml), N,N-dimethyloctylamine (4.96 g) added, and the mixture stirred at 65° for 24 hours. The polymer was then filtered off and washed with methanol and diethyl ether, and dried under vacuum to give N,N-dimethyl-N-octylammoniomethyl-substituted polystyrene, chloride salt, (4.35 g), (exchange capacity=2.17 m.eq. Cl−/g (b)=0.97 molar percent).

EXAMPLES 2–5

Chloromethylated polystyrenes containing 1% divinyl benzene as crosslinking agent and containing 2.58, 3.95, 4.91 and 5.96 m.eq. Cl/g were prepared from chloromethyl styrene, styrene and divinylbenzene as in Example 1. The above polymers were then reacted with N,N-dimethyloctylamine in DMF and worked up, as in Example 1, to give N,N-dimethyl-N-octylammoniomethyl-substituted polystyrene, chloride salt, with the following exchange capacities: 1.77, 2.34, 2.76, 3.15 m.eq. Cl−/g and (b) values of 0.93, 1.00, 1.08 and 1.17 molar percent respectively (Examples 2–5).

EXAMPLE 6

Chloromethylated polystyrene (1% cross-linked 4.91 m.eq. Cl/g), (1 g) as used in Example 4, was suspended in DMF (25 ml). N,N-dimethyldecylamine (1.8 g) added, and the mixture stirred at 70° for 24 hours. After work-up as in Example 1, the N,N-dimethyl-N-decylammoniomethyl-substituted polystyrene, chloride salt, was obtained as off-white beads (1.83 g) (exchange capacity=2.44 m.eq. Cl−/g, (b)=1.08 molar percent).

EXAMPLE 7

A 0.5% cross-linked chloromethylated polystyrene was prepared from chloromethylstyrene (31.29 g). styrene (18.25 g), and divinylbenzene (0.46 g) by the method described in Example 1. After sieving 7.52 g of material of particle size, 53–106 μM, containing 3.89 m.e.q. Cl/g, was obtained. This polymer (2.0 g) was suspended in DMF (60 ml), N,N-dimethyloctylamine (3.87 g) added, and the mixture stirred at 65° for 24 hours. After work-up as in Example 1, N,N-dimethyl-N-octylammoniomethyl-substituted polystyrene, chloride salt, (3.00 g) was obtained (exchange capacity=2.23 m.eq. Cl−/q, (b)=0.51 molar percent).

EXAMPLE 8

A 2% cross-linked chloromethylated polystyrene was prepared from chloromethylstyrene (32.7 g), styrene (16.99 g) and divinylbenzene (1.82 g) by the method described in Example 1. After sieving 25.4 g of material of particle size, 53–106 μM, containing 3.86 m.eq. Cl/g, was obtained. This polymer (5 g) was reacted with N,N-dimethyloctylamine (5 g), DMF (80 ml) at 80° for 48 hours to give, after work-up as in Example 1, N,N-dimethyl-N-octylammoniomethylated-substituted polystyrene, chloride salt, (7.75 g) (exchange capacity=2.51 m.eq. Cl−/g (b)=0.98 molar percent).

EXAMPLES 9–16, 18–21 and 25–32

A commercially aVailable 1% cross-linked chloromethylated polystyrene (3.72 m.eq. Cl−/g or 4.15 m.eq. Cl/g, 200–400 mesh) ("Bio Rad S-X1, chloromethylated") was used in these examples.

EXAMPLES 9–13

N,N-dimethylhexylamine, N,N-dimethyloctylamine, N,N-dimethyldecylamine, N,N-dimethyldodecylamine, and N,N-dimethyltetradecylamine were each reacted with the above chloromethylated polystyrene (1% cross-linked, 3.72 m.eq. Cl−/g) in DMF at 70° to give, after work up as described in Example 1, the corresponding N,N-dimethyl-N-alkylammoniomethyl-substituted polystyrenes, chloride salts, with the following exchange capacities:- Example 9, hexyl, 2.62 m.eq. Cl−/g; Example 10, octyl, 2.40 m.eq. Cl−/g; Example 11, decyl, 2.21 m.eq. Cl−/g; Example 12, dodecyl, 2.11 m.eq. Cl−/g; Example 13, tetradecyl, 2.02 m.eq. Cl−/g. For each of these examples (b) was 0.9 molar percent.

EXAMPLE 13A

Chloromethylpolystyrene (33.0 Kg) was washed twice with dichloromethane (2×340 L) and stirred with N-methylpyrrolidone (815 L) that had been purged under an atmosphere of nitrogen for 1 hour at 50°. The mixture was warmed to 60–65° and N,N-dimethyldodecylamine (81.6 Kg) added. It was then further warmed to 65–70° for 5 hours. The mixture was cooled to 55–60° and the product isolated by centrifugation. The wet product was reslurried with a mixture of N-methylpyrrolidone (250 L) and dichloromethane 250 L), then dichloromethane (500 L), followed by a mixture of dichloromethane (450 L) and ethyl acetate (450 L). The product was then further washed with ethyl acetate (2×910 L) and vacuum dried for 24 hours at room temperature followed by 50° for 72 hours, to afford N,N-dimethyl-N-dodecylammoniomethyl-susbtituted polystyrene chloride.

EXAMPLE 14

Ethylchloroformate (18.3 ml) was added slowly to a solution of heptanoic acid (20.0 g) and triethylamine (26.7 ml) in tetrahydrofuran (250 ml), maintained at −10°. The resulting mixture was stirred at 10° for 0.75 hour, cooled to 5° and a 33% solution of dimethylamine in ethanol (41.6 ml) added dropwise. This mixture was then allowed to warm to room temperature and stirred for 4 hours. The mixture was filtered and the filtrate evaporated to dryness. The residue was dissolved in chloroform (250 ml) and washed with 1% aqueous sodium carbonate solution (200 ml) and water, then dried and evaporated. The residual oil was chromatographed on silica gel to give N,N-dimethylheptanamide (14.1 g) as a colourless oil.

This amide (13.5 g) was treated with lithium aluminium hydride (4.88 g) in dry tetrahydrofuran (250 ml) to give, after work-up, N,N-dimethylheptylamine (7.10 g) as a colourless oil.

Chloromethylated polystyrene (3.0 g, 3.72 m.eq. Cl−/g) was suspended in DMF, N,N-dimethylheptylamine (3.7 g) added and the mixture heated at 75° for 24 hours. After work-up as described in Example 1, N,N-dimethyl-N-heptylammoniomethyl-substituted polystyrene, chloride salt, was obtained as an off-white resin (4.49 g), (exchange capacity=2.50 m.eq. Cl−/g, (b)=0.98 molar percent).

EXAMPLE 15

N,N dimethylnonylamine was prepared from nonanoic acid by the method described in Example 14.

A suspension of chloromethylated polystyrene (3.0 g, 3.72 m.eq. C−1/g) in DMF (50 ml) was treated with N,N-dimethylnonylamine (4.5 g) and the mixture stirred at 70° for 24 hours. Work-up as described in Example 1 gave N,N-dimethyl-N-nonylammoniomethyl-substituted polystyrene, chloride salt (4.72 g, exchange capacity=2.19 m.eq. Cl−/g, (b)=0.98 molar percent).

EXAMPLE 16

N,N-dimethylundecylamine was prepared from undecanoic acid by the method described in Example 14.

A suspension of chloromethylated polystyrene (2.0 g, 3.72 m.eq. C−1/g) in DMF was treated with N,N-dimethylundecylamine (5.0 g) at 70° for 28 hours. work-up as described in Example 1 gave N,N-dimethyl-N-undecylammoniomethyl-substitited polystyrene, chloride salt (3.38 g, exchange capacity=2.05 m.eq. Cl−/g, (b)=0.98 molar percent).

EXAMPLE 17

A 2% cross-linked, styrene-divinylbenzene copolymer, chloromethylated to give a Cl content of 4.45 m.eq. Cl−/g, (5 g) was treated with N,N-dimethyloctylamine (9.15 g) at 70° for 27 hours. After work-up as described in Example 1, N,N-dimethyl-N-octylammoniomethyl-substituted polystyrene, chloride salt, was obtained as yellow beads (8.26 g, exchange capacity=2.5 m.eq. Cl−g, (b)=1.61 molar percent).

EXAMPLE 18

Sodium borohydride (6.62 g) was added in portions to propionic acid (52.5 ml), cooled to 5°, maintaining the temperature below 20°. N-methyloctylamine (5 g) was added dropwise, keeping the temperature at 20°. The reaction was stirred at 80° for 3 hours, cooled and basified with 2N sodium hydroxide. The aqueous solution was extracted with dichloromethane (2×75 ml). The combined extracts were dried with anhydrous magnesium sulphate and evaporated to dryness. The resulting oil was purified by column chromatography to give N-methyl-N-propyloctylamine as a colourless oil (4.09 g, 63%).

To a suspension of chloromethystyrene-styrenedivinylbenzene co-polymer (1% w/w divinylbenzene, 4.15 m.eq Cl−/g) (2 g) in DMF (50 ml) the above amine was added and the mixture stirred at 70° for 24 hours to give, after washing and drying as in Example 1, the corresponding quaternised polymer as off-white resin beads (3.11 g) (exchange capacity=2.26 m.eq. Cl−/g, (b)=1 molar percent).

EXAMPLE 19

N-methyl-di-n-octylamine (14.26 g) was reacted with 1% cross-linked chloromethyl polystyrene (5 g, 18.6 mmoles) in DMF (125 ml) at 70° for 24 hours, to give after washing as in Example 1 the corresponding quaternised polymer as off-white resin beads (9.05 g) (exchange capacity=1.87 m.eq. Cl−/g, (b)=0.98 molar percent).

EXAMPLE 20

N,N-diethyloctylamine (13.7 g) was reacted with 1% cross-linked chloromethylstyrene-styrene-divinylbenzene co-polymer (10 g, 37 2 m.eq. Cl) in DMF (100 ml) at 80° for 12 hours. After work-up as in Example 1, the corresponding quaternised polymer was isolated as off-white resin beads (16.8 g) (exchange capacity=2 09 m.eq. Cl−/g, (b)=0.98 molar percent).

EXAMPLE 21

N,N-dibutyloctylamine was prepared from dibutylamine and octanoyl chloride by a method similar to that in Example 14.

This amine (17 g) was reacted with 1% cross-linked chloromethylstyrene-styrene-divinylbenzene co-polymer (10 g, 40.2 m.eq. Cl) in DMF (100 ml) at 80° for 1 hour. Work-up as in Example 1, gave the corresponding quaternised polymer as off-white resin beads (15.0 g) (exchange capacity=1.90 m.eq. Cl−/g, (b)=1 molar percent).

EXAMPLE 22

Chloromethylstyrene (50 g) in ethanol (100 ml) was added dropwise to 33% dimethylamine in i.m.s (500 ml) over 20 minutes and the temperature rose to 35°. The reaction was stirred at room temperature for 20 hours. 33% Dimethylamine in i.m.s (50 ml) was added and the reaction was heated at reflux for 30 minutes. The reaction was cooled and evaporated to dryness. The resulting product was dissolved in dichloromethane and washed with 2N hydrochloric acid (2×500 ml). The combined extracts were basified with 2N sodium hydroxide and extracted with dichloromethane (2×200 ml). The combined organic extracts were washed with water, dried with anhydrous magnesium sulphate and evaporated to dryness. More inhibitor was added and the oil was purified by distillation to give 3(4)-(N,N-dimethylaminomethyl)-styrene as a colourless oil. bp 66° at 0.1 Torr. (37 g, 78%).

The above amine (31.17 g), styrene (17.93 g), divinylbenzene (0.87 g) and azobisisobutyronitrile (AIBN) (0.5 g) were polymerised as in Example 1. After 7 hours the mixture was poured into distilled water. The resin formed was washed by decantation with cold and hot water, filtered and washed with acetone, ether and finally water. Drying under reduced pressure gave a 1% w/w cross-linked N,N-dimethylaminomethyl-substituted polystyrene polymer containing 3.85 m.eq. N/g (11.01 g, 53–106 μ, 22%).

The above cross-linked N,N-dimethylaminomethyl-substituted polystyrene (5 g) was suspended in DMF (100 ml), 1-iodododecane (15 g) was added and the reaction was stirred at 70° for 20 hours. The polymer was filtered off and washed with DMF and methanol. Anion exchange was accomplished by stirring the polymer in 2N HCl: MeOH (250 ml:250 ml) and standing overnight. The resin was then filtered off and washed with 2N HCl, water, methanol and ether. Finally dried under vacuum to give the corresponding quaternised polymer (4.26 g) (exchange capacity=1.82 m.eq. Cl−/g, 0.38 m.eq. I−/g, (b)=0.99 molar percent).

EXAMPLE 23

To a mixture of N-methyldodecylamine (49.5 g) and anhydrous potassium carbonate (18.1 g) in ethanol (200 ml) was added chloromethylstyrene (20 g) in ethanol (75 ml) over 20 minutes. The reaction was stirred at room temperature for 20 hours and heated at reflux for 45 minutes. The reaction mixture was evaporated to dryness and the residue was dissolved in 2N hydrochloric acid and extracted with chloroform (200 ml). The chloroform extract was washed with water, dried with anhydrous magnesium sulphate and evaporated to dryness. The oil was purified by chromatography giving 3(4)-(N-dodecyl-N-methylaminomethyl)styrene as an orange oil (27.5 g, 67%).

The above amine (11.46 g), styrene (3.22 g), divinylbenzene (0.33 g) and AIBN (0.2 g) were mixed to give a solution and then added to a solution of polyvinylalcohol (m.w. 125,000) (0.5 g) in distilled water (200 ml). The mixture was stirred at 80° under an atmosphere of nitrogen at such a rate as to maintain the monomers in suspension. After 7 hours the mixture was poured into distilled water. The resin was filtered off and washed with water. Product was transferred to a beaker and washed by stirring and decantation with acetone (2×200 ml) and ether (2×200 ml). The resin was filtered off and drying under reduced pressure gave a 2% w/w cross-linked N-dodecyl-N- methylaminomethyl-substituted polystyrene resin (10 g, 66%).

(c) The above 2% w/w cross-linked N-dodecyl-N-methylaminomethyl-substituted polystyrene (4 g) was suspended in DMF (50 ml) and stirred for 1 hour. Methyl iodide (1.75 ml) was added and the reaction was stirred at 60° for 22 hours. Additional methyl iodide (1.75 ml) was added at 19 hours. The polymer was filtered off and washed as in Example 22 to give, after drying under vacuum, the corresponding quaternised polymer (2.2 g, 106–212 μ) (exchange capacity=2.11 m.eq. Cl—/g, 0.065 m.eq. I—/g, (b)=1.99 molar percent).

EXAMPLE 24

To a mixture of N-methyloctylamine (25 g) and anhydrous potassium carbonate (13.3 g) in ethanol (150 ml) was added chloromethylstyrene (13.3 g) in ethanol (10 ml) over 15 minutes. The reaction was stirred at room temperature for 24 hours, filtered and the filtrate was evaporated to dryness. The residue was dissolved in dichloromethane and washed with water. The organic layer was then dried with anhydrous magnesium sulphate and evaporated to dryness. The oil was purified by chromatography (with hexane:dichloromethane as eluent) to give 3(4)-(N-octyl-N-methylaminomethy)styrene as an oil (11.5 g, 51%).

The above amine (11.02 g), styrene (3.61 g), distyrene (0.37 g) and AIBN (0.2 g), were polymerised as in Example 23 to give, after drying, a 2% w/w crosslinked N-octyl-N-methylaminomethyl-substituted polystyrene resin (10.45 g, 70%).

The above N-methyl-N-octylaminomethyl-substituted polystyrene (7 g) was suspended in DMF (100 ml), methyl iodide (5.3 ml) was added and the reaction was stirred at 60° for 9 hours. Additional methyl iodide (2 ml) was added at 5 hours. The polymer was filtered and washed as in Example 22 to give, after drying, the corresponding quaternised polymer (5.6 g) (exchange capacity=2.36 m.eq. Cl—/g, 0.10 m.eq. I—/g, (b)=1.99 molar percent).

EXAMPLE 25

Diamylketone (12 g) was hydrogenated at 50 psi in the presence of 10% Pd/C (1.5 g) and benzylamine (8.31 g) at room temperature for 6 hours. Further catalyst (1.5 g) was added and the mixture was hydrogenated at 40° for 5 hours. The reaction mixture was filtered and evaporated to dryness (combined with the product from a previous 12 g hydrogenation). The oil was purified by column chromatography to give 6-undecylamine as an oil (9.1 g, 38%).

To 90% formic acid (11.9 ml), cooled to −5°, was added the above amine (9.6 g), dropwise over 45 minutes keeping the temperature below 5°. 37% Formaldehyde (10 ml) was then added to the cooled reaction before heating at reflux for 6 hours. Concentrated hydrochloric acid (4 ml) was added and the reaction mixture was evaporated to dryness. The resulting oil was scratched under ethyl acetate to give a green solid. The solid was collected by filtration but this waxy solid rapidly became an oil on drying. This oil was dissolved in water, basified with sodium carbonate. The aqueous phase was extracted with ethyl acetate. The extracts were washed with water, dried with anhydrous magnesium sulphate and evaporated to dryness. The oil was distilled at 0.1 torr/250° in a Kugelrohr apparatus to give 6-(dimethylamino)undecane as a colourless oil (4.06 g, 36%).

The above amine (3 g) was reacted with 1% crosslinked chloromethylated polystyrene (2 g, 7.44 mmoles) in DMF (50 ml) at 70° for 20 hours to give, after washing and drying as in Example 1, the corresponding quaternised polymer as off-white resin beads (2.96 g) (exchange capacity=2.00 m.eq. Cl—/g, (b)=0.98 molar percent).

EXAMPLE 26

To a solution of potassium t-butoxide (34.68 g) in anhydrous diethyl ether (750 ml), under nitrogen, 7-carboxyheptyltriphenylphosphonium bromide (75 g) was added and the mixture was heated at reflux for 2 hours. The diethyl ether was removed by distillation and 6-undecanone (40 g) was added over 10 minutes. After 30 minutes, anhydrous diethyl ether (200 ml) was added to aid stirring. The mixture was heated at reflux for 2 hours, cooled and acidified with 2N HCl. The aqueous solution was extracted with dichloromethane (300 ml). The organic extracts were combined and washed with 2N NaOH (2×200 ml). The aqueous extracts were acidified with 2N HCl and extracted with dichloromethane (2×200 ml). The organic extracts were combined, dried with anhydrous magnesium sulphate and evaporated to dryness. The resulting oil was triturated with light petroleum. The light brown precipitate was removed by filtration and the filtrate was evaporated to dryness. The oil was purified by column chromatography to give 9-pentyl-8-tetradecenoic acid as an oil (13.94 g, 30.4%).

To a solution of the above acid (13.8 g) and triethylamine (7.8 ml) in dry tetrahydrofuran (200 ml), cooled to 5°, was added ethyl chloroformate (5.4 ml) dropwise over 15 minutes. The reaction mixture was stirred at 10° for 2 hours. 33% Dimethylamine in industrial methylated spirits (125 ml) was added keeping the temperature at 10°. The reaction mixture was then stirred at room temperature for 4 hours and evaporated to dryness. The resulting oil was dissolved in diethyl ether and washed with 1N NaOH, water and then dried with anhydrous magnesium sulphate and evaporated to dryness. (This was then combined with the product from a previous reaction of the above acid (10.4 g). The oil was purified by column chromatography (with dichloromethane as eluent) to give 9-pentyl-8-tetradecenamide as a coloured oil (14.91 g, 57%).

The above amide (14.6 g) in dry tetrahydrofuran was added dropwise to a suspension of lithium aluminium hydride (2.6 g) in dry tetrahydrofuran (150 ml), under an atmosphere of nitrogen. The temperature rose to 38° during the addition. The reaction was stirred at room temperature for 1.5 hours and heated at reflux for 1 hour. The reaction was cooled and water (2.6 ml), 15% aq. sodium hydroxide (2.6 ml), water (7.8 ml) were added. The reaction was stirred for 1 hour and then filtered. The filtrate was evaporated to dryness. The oil was purified by distillation to give 1-dimethylamino-9-pentyl 8-tetradecene as an oil (bp 0.01 torr, 161-168°) (10.79 g, 77%).

The above amine (3 g) was reacted with 1% crosslinked chloromethylated polystyrene (1.5 g, 6.23 mmoles) in DMF (60 ml) at 60° for 21 hours to give, after washing and drying as in Example 1, the corresponding quaternised polymer as off-white resin beads (3.18 g) (exchange capacity=1.88 m.eq. Cl—/g (b)=1 molar percent).

EXAMPLE 27

1-Dimethylamino-9-pentyl-8-tetradecene (Example 26c) (7.5 g) was hydrogenated in ethanol (75 ml) at 45 psi in the presence of 10% Pd/C (0.7 g) at room temperature for 5 hours. The reaction mixture was filtered and evaporated to dryness. The resulting oil was purified by distillation at 0 01 torr (in a Kugelrohr apparatus at 210°) to give 1-dimethylamino-9-pentyltetradecane as a colourless oil (5.7 g, 76%).

The above amine (5.5 g) was reacted with 1% cross-linked chloromethylated polystyrene (3 g, 12.45 mmoles) in DMF (100 ml) and methanol (20 ml) at 60° for 28 hours to give, after washing and drying as in Example 1, the corresponding quaternised polymer as off-white resin beads (6.6 g) (exchange capacity=1.81 m.eq. Cl−/g, (b)=1 molar percent).

EXAMPLE 28

Geranylbromide (20 g) in ethanol (50 ml) was added to 33% dimethylamine in industrial methylated spirits (240 ml) and the mixture was heated at reflux for 8 hours. The reaction mixture was evaporated to dryness, mixed with 2N sodium hydroxide (50 ml) and then extracted with diethyl ether (2×100ml). The ether extracts were combined and washed with water (50 ml), then dried with anhydrous magnesium sulphate and evaporated to dryness. The resulting orange oil was purified by chromatography (with a gradient $CH_2Cl_2$:MeOH system as eluent) to give 1-dimethylamino-3.7-dimethyl-2,6-octadiene as an oil (12.1 g, 72%).

The above amine (3.76 g) was reacted with 1% cross-linked chloromethylated polystyrene (2 g, 8.3 mmoles) in DMF at 70° for 20 hours to give, after washing and drying as in Example 1, the corresponding quaternised polymer as off-white resin beads (3.1 g) (exchange capacity=2.44 m.eq. Cl−/g, (b)=1 molar percent).

EXAMPLE 29

1-Dimethylamino-3.7-dimethyl-2 6-octadiene (Example 28a) (12 g was hydrogenated in ethanol (100 ml) at 40 psi in the presence of 10% Pd/C (1.2 g) at room temperature for 5 hours. The reaction mixture was filtered and evaporated to dryness. The residue was dissolved in 2N sodium hydroxide and extracted with diethyl ether (2×100 ml). The ether extracts were combined and washed with water, dried with anhydrous magnesium sulphate and evaporated to dryness. The oil was purified by chromatography (10:1 dichloromethane:methanol as eluent) to give 1-dimethylamino-3,7-dimethyloctane as a wax (7.14 g, 60%).

(b) The above amine (3 g) was reacted with 1% cross-linked chloromethylated polystyrene (2 g, 8.3 mmoles) in DMF (60 ml) at 70° for 24 hours to give, after washing and drying as in Example 1, the corresponding quaternised polymer as off-white resin beads (3.24 g) (exchange capacity=2.31 m.eq. Cl−/g, (b)=1 molar percent).

EXAMPLE 30

To 90% formic acid (24.2 ml), cooled to 10°, was added isoamylamine (10 g) in portions keeping the temperature below 20°. 37% Formaldehyde (20 ml) was added to the cooled reaction mixture. The reaction was then heated at 70° for 6 hours. The reaction mixture was cooled and concentrated sulphuric acid (2 mole equivalents) was added and the reaction mixture evaporated to dryness. Isopropanol (25 ml) was added to the oil with cooling and this was diluted with anhydrous diethyl ether. The resulting thick, white precipitate was collected by filtration and washed with cold anhydrous diethyl ether. This was quickly dried under reduced pressure but gave an oil. Sucked dry at 0.01 torr for 24 hours and this gave 1-dimethylamino-3-methylbutane as the sulphate salt (11.1 g, 45%).

The above amine sulphate salt (4.5 g) was reacted with 1% cross-linked chloromethylated polystyrene (2 g, 7.44 mmoles) and anhydrous potassium carbonate (4.1 g) in DMF 50 ml) at room temperature for 24 hours and at 60° for 20 hours. The product was filtered off and washed with DMF, methanol, water, 2N hydrochloric acid, water, methanol and ether to give, after drying under reduced pressure, the corresponding quaternised polymer as off-white resin beads (2.28 g, exchange capacity=2.76 m.eq. Cl−/g, (b)=0/98 molar percent).

EXAMPLE 31

3 -Pentylamine (20 g) was added to 90% formic acid (48.4 ml). cooled to 0°, keeping the temperature below 10°, followed by 37% formaldehyde (40 ml). The reaction mixture was heated at reflux for 7 hours, cooled and concentrated hydrochloric acid (2 mole equivalents) was added. The reaction mixture was evaporated to dryness. Isopropanol (25 ml) was added and the solution was cooled and diluted with anhydrous diethyl ether. The resulting cream coloured solid was collected by filtration and dried under reduced pressure giving 3-dimethylaminopentaneethylpropane hydrochloride as a cream powder (m.p. 144–145°) (26.1 g, 75%).

The above amine (9 g) was reacted with 1% cross-linked chloromethylated polystyrene (4 g, 16.6 mmoles) and anhydrous potassium carbonate (8.2 g) as in Example 30(b) to give the corresponding quaternised polymer (5.12 g) (exchange capacity=2.30 m.eq. Cl−/g, (b)=1 molar percent).

Example 32

N,N-dimethylheptadecylamine (b.p. 117° @ 0.15 mmHg) was prepared from dimethylamine and heptadecanoic acid by the method described in Example 14.

This amine (11.7 g) was reacted with 1% cross linked chloromethylstyrene-styrene-divinylbenzene copolymer 5 g, 21 m.eq. Cl) in DMF (100 ml) at 80° for 12 hours. Work-up as in Example 1 gave the corresponding quaternised polymer as off-white resin beads (9.78 g) (exchange capacity=1.93 m.eq. Cl−/g, (b)=1 molar percent).

EXAMPLE A

A liquid formulation for oral administration is prepared from the following:

|  | (w:v) |
| --- | --- |
| Compound of Example 12 | 10% |
| Avicel RC591 | 1.25% |
| Antifoam emulsion | 0.05% |
| Flavours | 0.02% |
| Sodium saccharide | 0.01% |
| Preservatives: |  |
| Methyl Parabenz | 0.12% |
| Propyl Parabenz | 0.04% |
| Sorbitol syrup (70%) | 30% |
| Glycerin | 5% |
| Water | to 100% |

EXAMPLE B

A capsule formulation for oral administration is prepared by incorporating the following into a soft gelatin capsule:

Compound of Example 12 (500 mg), Aerosil 200 (5 mg), Magnesium Stearate (5 mg), Avicel PH101 (40 mg), and, optionally, sodium starch glycollate (10 mg).

EXAMPLE C

A food additive formulation for example a sachet for reconstitution or mixing with food, is prepared by incorporating into a powder formulation, compound of Example 12 (2500 mg), sodium carboxymethylcellulose (50 mg), sucrose (2400 mg) and flavours (50 mg).

BIOLOGICAL DATA

In the binding assays the polymers used contained 5-15% $H_2O$ w/w. and all weights used in the assays refer to these undried materials.

EQUILIBRIUM BINDING OF BILE ACIDS (AS SODIUM SALTS) TO RESINS

The compounds of the examples (10 mg/tube) were incubated with a range of $^{14}C$ radiolabelled sodium taurochenodeoxycholate (TCDC) or sodium glycocholate (GC) solutions (0.05 mM-24 mM) of known specific activity, in Krebs Henseleit buffer (2.5 ml final volume). The resin was allowed to equilibrate with the bile salt solution for a period of three hours at 37° in a shaking water bath. The resin was removed from the incubation medium by centrifugation (15 minutes at 3,000 g). The radioactivity of the supernatant was determined, and from this the free and bound quantities of bile salt were calculated. These were expressed as moles of bile salt bound per gram of resin.

RESULTS

The compounds of examples 1-32 at a concentration of 5.7mM GC were found to bind in the range of from 0.63 to 1.24 mmoles GC per gram weight of resin; and at a concentration of 5.7mM TCDC were found to bind in the range of from 0.53 to 1.34mmoles TCDC per gram weight of resin.

IN VITRO DISSOCIATION ASSAYS

In the method of Table I of test compound (20 mg) was shaken in Krebs' buffer for 3 hours in the presence of 5mM sodium [$^{14}C$] glycocholate (5 ml). In the method of Table 2, test compound (150 mg) was equilibrated with 5 mM sodium glycocholate (30 ml) in the same buffer. The compound was separated by centrifugation and the total bound determined by subtraction of the amount in the supernatant from the total bile acid used. Dissociation was measured either by continuous perfusion of the preloaded compound with Krebs' buffer and determination of the radioactivity in the perfusate (Table 1) or by resuspending the compound in Krebs' buffer, shaking and sampling the mixture through a filter at several time points up to 20 minutes. Radioactivity and hence bile acid dissociated was determined in the filtrate (Table 2).

TABLE 1

| | In vitro dissociation - continuous. | |
|---|---|---|
| | GC Bound (mmoles/g) | |
| Example | t = 0 | t = 2h |
| Cholestyramine | 0.86 | 0.11 |
| 1 | 0.94 | 0.31 |
| 2 | 0.75 | 0.34 |
| 3 | 0.92 | 0.28 |
| 4 | 0.94 | 0.26 |
| 5 | 0.92 | 0.22 |
| 6 | 0.95 | 0.38 |
| 7 | 1.02 | 0.38 |
| 8 | 0.92 | 0.25 |
| 9 | 0.95 | 0.24 |

TABLE 1-continued

| | In vitro dissociation - continuous. | |
|---|---|---|
| | GC Bound (mmoles/g) | |
| Example | t = 0 | t = 2h |
| 10 | 0.98 | 0.34 |
| 11 | 0.83 | 0.47 |
| 12 | 0.78 | 0.53 |
| 13 | 0.94 | 0.49 |
| 14 | 0.95 | 0.21 |
| 15 | 0.95 | 0.37 |

TABLE 2

| | In vitro dissociation - equilibrium. | |
|---|---|---|
| | GC Bound (mmoles/g) | |
| Example | t = 0 | t = 2 min |
| Cholestyramine | 0.76 | 0.42 |
| 9 | 0.76 | 0.71 |
| 10 | 0.80 | 0.74 |
| 11 | 0.83 | 0.76 |
| 12 | 0.82 | 0.76 |
| 16 | 0.81 | 0.75 |
| 18 | 0.81 | 0.74 |
| 20 | 0.63 | 0.55 |
| 21 | 0.77 | 0.75 |
| 22 | 0.74 | 0.69 |
| 23 | 0.74 | 0.71 |
| 24 | 0.78 | 0.71 |
| 26 | 0.77 | 0.73 |
| 27 | 0.72 | 0.68 |
| 31 | 0.73 | 0.58 |

What is claimed is:

1. A crosslinked polystyrene polymer of structure (I)

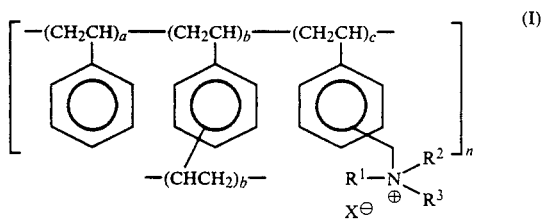

in which, $R^1$ is a saturated or unsaturated $C_8$ to $C_{20}$ alkyl group;

$R^2$ and $R^3$ are the same or different and are each $C_{1-4}$alkyl;

$X-$ is a physiologically acceptable counter ion;

a, b and c are numbers which indicate the relative molar percentages of the units present in a random distribution in said polymer, (b) being from about 0.5 to about 10 molar percent, and (c) being from about 30 to about 99 molar percent; and n is a number indicating the number of repeating units in said polymer.

2. A polystyrene polymer as claimed in claim 1 in which $R^1$ is a saturated $C_8$ to $C_{14}$ alkyl group, and $R^2$ and $R^3$ are each methyl.

3. A polystyrene polymer as claimed in claim 2 in which (b) is from about 1 to about 4 molar percent of said polymer.

4. A polystyrene polymer as claimed in claim 1 which is N,N,dimethyl-N-nonylammoniomethyl-substituted polystyrene, chloride salt.

5. A polystyrene polymer as claimed in claim 1 which is N,N,dimethyl-N-octylammoniomethyl-substituted polystyrene, chloride salt.

6. A polystyrene polymer as claimed in claim 1 which is N,N,dimethyl-N-decylammoniomethyl-substituted polystyrene, chloride salt.

7. A polystyrene polymer as claimed in claim 1 which is N,N,dimethyl-N-undecylammoniomethyl-substituted polystyrene, chloride salt.

8. A polystyrene polymer as claimed in claim 1 which is N,N,dimethyl-N-dodecylammoniomethyl-substituted polystyrene, chloride salt.

9. A pharmaceutical composition comprising a polystyrene polymer of structure (I) as claimed in claim 1 in association with a pharmaceutically acceptable carrier.

10. A pharmaceutical composition according to claim 9, in which, in the compound of structure (I) $R^1$ is a saturated $C_8$ to $C_{14}$ alkyl group and $R^2$ and $R^3$ are each methyl.

11. A pharmaceutical composition according to claim 10 in which, in the compound of structure (I) (b) is from about 1 to about 4 molar percent.

12. A pharmaceutical composition according to claim 11 in which the compound of structure (I) is N,N,dimethyl-N-nonylammoniomethyl-substituted polystyrene, chloride salt.

13. A pharmaceutical composition according to claim 11 in which the compound of structure (I) is N,N,dimethyl-N-octylammoniomethyl-substituted polystyrene, chloride salt.

14. A pharmaceutical composition according to claim 11 in which the compound of structure (I) is N,N,dimethyl-N-decylammoniomethyl-substituted polystyrene, chloride salt.

15. A pharmaceutical composition according to claim 11 in which the compound of structure (I) is N,N,dimethyl-N-undecylammoniomethyl-substituted polystyrene, chloride salt.

16. A pharmaceutical composition according to claim 11 in which the compound of structure (I) is N,N,dimethyl-N-dodecylammoniomethyl-substituted polystyrene, chloride salt.

* * * * *

UNITED STATES PATENT AND TRADEMARK OFFICE
CERTIFICATE OF CORRECTION

PATENT NO. : 4,954,339

DATED : September 4, 1990

INVENTOR(S) : Albert A. Jaxa-Chamiec, Deirdre M. B. Hickey

It is certified that error appears in the above-identified patent and that said Letters Patent is hereby corrected as shown below:

On page 16, line 20, Claim 1, replace "X-," with --- $X^-$ ---.

Signed and Sealed this

Twenty-first Day of July, 1992

Attest:

DOUGLAS B. COMER

*Attesting Officer*  *Acting Commissioner of Patents and Trademarks*